United States Patent [19]

Rathgeb

[11] 4,154,826

[45] May 15, 1979

[54] THIOPHOSPHORYLGUANIDINES FOR COMBATING PESTS

[75] Inventor: Paul Rathgeb, Basel, Switzerland

[73] Assignee: Ciba-Geigy Corporation, Ardsley, N.Y.

[21] Appl. No.: 862,694

[22] Filed: Dec. 21, 1977

[30] Foreign Application Priority Data

Dec. 30, 1976 [CH] Switzerland ............... 16474/76
Mar. 4, 1977 [CH] Switzerland ............... 2722/77
Sep. 12, 1977 [CH] Switzerland ............... 11115/77

[51] Int. Cl.$^2$ .................... A01N 9/36; C07F 9/24
[52] U.S. Cl. ............................ 424/211; 260/944; 260/945
[58] Field of Search ............... 260/944, 940, 945; 424/211

[56] References Cited

U.S. PATENT DOCUMENTS 4,006,203  2/1977  Chance et al. ............... 260/940 OR

OTHER PUBLICATIONS

Houben–Weyl, "Method der Organischen Chemie", vol. 12, No. II, p. 520.

Primary Examiner—Anton H. Sutto
Attorney, Agent, or Firm—Harry Falber

[57] ABSTRACT

Thiophosphorylguanidines as hereinafter defined in formula are effective for combating pests, such as insects, Acarina, microorganisms, and preferably phytopathogenic nematodes. The new compounds act systemically.

21 Claims, No Drawings

THIOPHOSPHORYLGUANIDINES FOR COMBATING PESTS

The present invention relates to thiophosphorylguanidines which correspond to one of the tautomeric formulae I

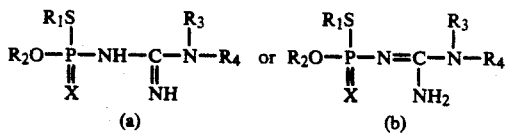

wherein
- $R_1$ represents $C_3$–$C_5$-alkyl,
- $R_2$ represents methyl or ethyl,
- $R_3$ and $R_4$ independently of one another represent hydrogen, $C_1$–$C_8$-alkyl, CN, —$CONH_2$ or $C_2$–$C_8$-acyl, and
- X represents oxygen or sulphur, to processes for producing these compounds, and also to compositions and processes for combating nematodes, insects, Acarina and microorganisms.

By alkyl are meant, depending on the given number of carbon atoms, for example the following groups: methyl, ethyl, propyl, isopropyl, butyl, isobutyl, sec.-butyl, tert.-butyl, as well as the isomeric amyl, hexyl, heptyl and octyl groups. $C_2$-acyl denotes the acetyl group. $C_3$–$C_8$-acyl denotes an organic group having 2 to 7 carbon atoms, which is also bound by way of a —CO— bridge to the radical of the molecule. Examples which may be mentioned are propionyl, butyryl, valeryl, pivaloyl, caproyl, heptoyl, capryl and benzoyl. However, $C_3$–$C_8$-acyl groups are also derivable from isomers of these acids, or from cycloalkanecarboxylic acids such as cyclopropanecarboxylic acid.

Other tautomeric forms of the compounds of the formula I can be for example in the form (c), if $R_3$ represents hydrogen:

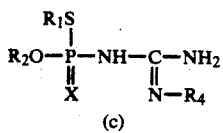

In which of the different tautomeric forms an individual compound of the formula I mainly occurs depends on various factors. The present invention relates to all isomers of the formula I. With respect to the pictorial presentation of a compound of the formula I, the given formula in each case is representative of all the possible isomeric structures.

The compounds of the formula I can be produced according to the invention in the following manner:

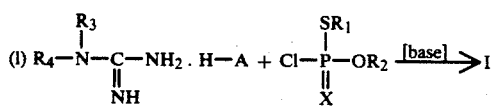

or (2) if X represents oxygen:

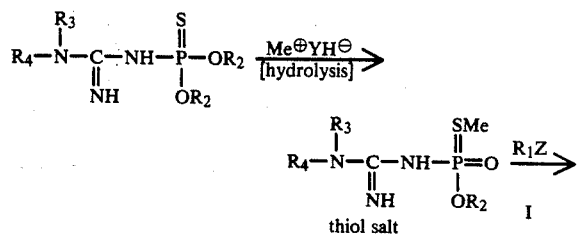

wherein $R_1$ to $R_4$ and X have the meanings given for the formula I, Z represents halogen, preferably chlorine, bromine or iodine, or alternatively a sulphate group, Me represents alkali metal, alkaline-earth metal or $NH_4$, Y represents oxygen or sulphur, and A represents any desired acid radical of customary acids (hydrohalic acid, particularly HCl, sulphuric acid, phosphoric acid, nitric acid, etc.). This acid radical is, as is known, not of importance with regard to the course of the reaction.

In process (1) involving amidation of a mono- or di-thiophosphoric acid ester chloride, reaction temperatures of 0° to 100° C., preferably 10°–45° C., are applied.

The reactions are performed in solvents or diluents which are inert to the reactants. The following are for example suitable: aliphatic or aromatic hydrocarbons such as benzene, toluene, xylenes or petroleum ether; halogenated hydrocarbons such as chlorobenzene, methylene chloride, ethylene chloride or chloroform; ethers and ethereal compounds such as dialkyl ether, dioxane or tetrahydrofuran; nitriles such as acetonitrile; N,N-dialkylated amides such as dimethylformamide; water; ketones such as methyl ethyl ketone, dimethylsulphoxide, and mixtures of such solvents with each other. Particularly preferred are two-phase reaction mediums, e.g. methylene chloride/water.

Reaction (1) is performed in the presence of an acid-binding agent or condensation agent. The following are suitable: tertiary amines such as trialkylamines (e.g. triethylamine), pyridine and pyridine bases, or inorganic bases, such as the oxides and hydroxides, hydrogen carbonates and carbonates of alkali metals and alkaline-earth metals as well as sodium acetate (see German Offenlegungsschrift No. 2,451,911). It is also possible to use an excess of the employed guanidine.

Process (2) involving transesterification of an amidinophosphoric acid thiono ester is performed in the temperature range of 20°–100° C., in water as the necessary solvent of the hydrolysis stage. Also suitable however are mixtures of water and an immiscible solvent, such as a hydrocarbon (e.g. benzene) or chlorinated hydrocarbon (e.g. chloroform), in the sense of a phase-transfer method. In this case, the simultaneous use of quaternary ammonium salts, such as tetrabutylammonium bromide, is advantageous.

In the second reaction stage, entailing alkylation of the formed thiol salt, nonaqueous polar solvents, such as acetonitrile or dimethylformamide, are employed (see U.S. Pat. No. 3,896,193).

The guanidine derivatives and phosphoric acid thiol ester chlorides used as starting products are known, or they can be obtained by methods that are generally known [see Houben-Weyl "Methoden der organischen Chemie" (Methods in organic Chemistry), Vol. Phosphorverb. (Phosphorus compounds) II, p.519 ff.].

Phosphorylated formamidines are already known from German Offenlegungsschrift No. 2,312,738 and Offenlegungsschrift No. 2,451,911. Their nematocidal action is however very unsatisfactory. Furthermore, they do not have that high level of soil stability which is essential for combating soil pests.

It has now been shown that the compounds of the formula I of the present invention satisfy to a high degree the two requirements mentioned above. This is particularly surprising since directly homologous compounds display these properties only to a negligible extent.

Compounds of the formula I are stable under neutral and slightly alkaline conditions, and have in the soil a prolonged action against nematodes. Compounds of the formula I are effective in particular against nematodes of the phytopathogenic type; among these nematodes are to be mentioned the following genera: Meloidogyne, Radopholus, Pratylenchus, Ditylenchus, Heterodera, Paratylenchus, Belonolaismus, Trichodorus and Longidorus. The special advantage of these compounds is their systemic action, which enables the pests to be combated not only by means of soil treatment but also by means of leaf application through the plant to be protected (basipetal transport).

Advantageous compositions are those which enable a uniform distribution of the active substance throughout a layer of soil extending to a depth of 10 to 20 cm to be ensured. The manner and form of application are dependent in particular on the type of plant, on the climate and on the conditions of the soil. Since the novel active substances are as a rule not phytotoxic and do not impair the capability of germinating, they can be applied usually, without observance of a "waiting period," immediately before or after the sowing of the plants. It is likewise possible to treat already existing crops of plants with the novel compositions. In addition, for the purpose of effecting an increase, specific parts of plants, such as seeds, sections of stalk (sugar-cane) or bulbs, as well as roots or seedlings, can be dressed with dispersions or solutions of the active substances.

Besides having a nematocidal action, the compounds of the formula I also have an insecticidal and acaricidal action. They can thus be used against insects present in useful crops, especially against leaf insects, such as Anthonomus and Dysdercus, and also against various Acarina species.

A number of the compounds of the formula I have a phytobactericidal action.

An important group of active substances are those of the formula I wherein
$R_1$ represents $C_3$–$C_5$-alkyl,
$R_2$ represents methyl or ethyl,
$R_3$ and $R_4$ independently of one another represent hydrogen, $C_1$–$C_8$-alkyl, or one of the substituents —CN, —CONH$_2$ or $C_2$–$C_8$-acyl, and
X represents oxygen.

Another important group of active substances are those of the formula I wherein
$R_1$ represents $C_3$–$C_5$-alkyl,
$R_2$ represents ethyl,
$R_3$ represents hydrogen,
$R_4$ represents hydrogen, $C_1$–$C_8$-alkyl, —CN or $C_2$–$C_8$-acyl, and
X represents sulphur.

The following types of substituents and combinations of these with each other are preferred:
for $R_1$—$C_3$–$C_4$-alkyl, e.g. n-propyl;
for $R_2$—ethyl;
for $R_3$—hydrogen; and
for $R_4$—the CN groups.

The latter substituent combination is preferred for active substances of the formula I in which X represents oxygen.

Amongst the active substances particularly preferred, the following compounds of the formula I are to be mentioned:
N-(S-n-propyl-O-ethyl-dithiophosphoryl)-guanidine,
N-(S-sec.-butyl-O-ethyl-dithiophosphoryl)-guanidine,
N-(S-n-propyl-O-ethyl-thiophosphoryl)-guanidine,
N-(S-sec.-butyl-O-ethyl-thiophosphoryl)-guanidine,
N-(S-n-propyl-O-ethyl-dithiophosphoryl)-N'-cyanoguanidine,
N-(S-sec.-butyl-O-ethyl-dithiophosphoryl)-N'-cyanoguanidine,
N-(S-n-propyl-O-ethyl-thiophosphoryl)-N'-cyanoguanidine,
N-(S-sec.-butyl-O-ethyl-thiophosphoryl)-N'-cyanoguanidine,
N-(S-sec.-butyl-O-ethyl-thiophosphoryl)-N'-ethyl-guanidine, and
N-(S-n-propyl-O-ethyl-dithiophosphoryl)-N'-sec.-butylguanidine.

Compounds of the formula I can be used on their own or together with suitable carriers and/or additives. Suitable carriers and additives can be solid or liquid and they correspond to the substances common in formulation practice, e.g. natural or regenerated mineral substances, solvents, dispersing agents, wetting agents, adhesives, thickeners, binders and/or fertilisers. For widening their sphere of action, the compounds of the formula I can be combined with known insecticides, acaricides or nematocides, as well as with fungicides, herbicides, molluscicides or rodenticides.

The content of active substance in commercial compositions is between 0.1 and 90%.

For application, the compounds of the formula I can be in the following forms (the weight-percentage figures in brackets signify advantageous amounts of active substance):

solid preparations:
dust and scattering agents (up to 10%), granulates [coated granules, impregnated granules and homogeneous granules] (1 to 80%);

liquid preparations:
(a) water-dispersible concentrates of active substance: wettable powders and pastes (25 to 90% in the commercial packing, 0.01 to 15% in ready-for-use solutions); emulsion concentrates and solution concentrates 10 to 50%, 0.01 to 15% in ready-for-use solutions);
(b) solutions (0.1 to 20%); aerosols.

The following Examples illustrate the invention without in any way limiting the scope thereof. Temperature values are given in degrees Centigrade, and percentages relate to weight.

PRODUCTION EXAMPLES

EXAMPLE 1

8.4 g (0.1 mole) of dicyanodiamide is dissolved in 50 ml of 4 N NaOH solution (0.2 mole) and diluted with 50 ml of acetone. To this solution is added dropwise 21.8 g of S-n-propyl-O-ethyl-dithiophosphoric acid chloride dissolved in a small amount of acetone, the addition being made in such a manner that the temperature does not exceed 45°. The clear solution is stirred for 30 minutes, and then diluted with 250 ml of ice water. The product is subsequently precipitated by acidification with acetic acid to pH=5, and is filtered off after standing for one hour in an ice bath. The air-dried product is recrystallised from toluene to yield 18.4 g (69% of theory) of N-(S-n-propyl-O-ethyl-dithiophosphoryl)-N'-cyanoguanidine, m.p. 108°–110° [Compound No. 1].

EXAMPLE 2

43.6 g (0.2 mole) of S-n-propyl-O-ethyl-dithiophosphoric acid chloride is dissolved in 300 ml of methylene chloride, and added to a solution of 19.1 g (0.2 mole) of guanidine hydrochloride in 180 ml of water. There is then added dropwise with vigorous stirring at 20°, in the course of 15 minutes, a solution of 16 g of sodium hydroxide in 80 ml of water; and stirring is continued at 20° overnight. The product which has precipitated is filtered off and dried in air. Recrystallisation from toluene yields 33 g (68.5% of theory) of N-(S-n-propyl-O-ethyl-dithiophosphoryl)-guanidine, m.p. 123°–126° [Compound No. 2].

EXAMPLE 3

8.4 g (0.1 mole) of dicyanodiamide is dissolved in 50 ml of 4 N NaOH solution (0.2 mole) and diluted with 50 ml of acetone. To this solution is added dropwise 20.3 g of S-n-propyl-O-ethyl-thiophosphoric acid chloride dissolved in a small amount of acetone, the addition being effected in such a manner that the temperature does not exceed 45°. The clear solution is stirred for 30 minutes and is then diluted with 250 ml of ice water. The product is subsequently precipitated by acidification with acetic acid to pH=5–6, and, after standing for one hour in an ice bath, filtered off. The air-dried product is then recrystallised from ethyl acetate to yield 18 g (72% of theory) of N-(S-n-propyl-O-ethyl-thiophosphoryl)-N'-cyanoguanidine, m.p. 142°–144° [Compound No. 12].

EXAMPLE 4

40.5 g (0.2 mole) of S-n-propyl-O-ethyl-thiophosphoric acid chloride is dissolved in 300 ml of methylene chloride, and added to a solution of 19.1 g (0.2 mole) of guanidine hydrochloride in 180 ml of water. There is then added dropwise at 20° with vigorous stirring, within 15 minutes, a solution of 16 g of sodium hydroxide in 80 ml of water; and stirring at 20° is maintained for a further 3 hours. The organic phase is separated, washed twice with 50 ml of water, dried, and then concentrated in vacuo. The oily residue solidifies on treatment with ether to form a white crystal powder. There is obtained about 20.6 g (46% of theory) of N-(S-n-propyl-O-ethyl-thiophosphoryl)-guanidine, m.p. 105°–107° [Compound No. 15].

EXAMPLE 5

65 g (0.3 mole) of S-sec.-butyl-O-ethyl-thiophosphoric acid chloride is dissolved in 600 ml of toluene, and added to a solution of 40.8 g (0.3 mole) of ethyl-guanidinesulphate in 300 ml of water. There is then added at 20°, with vigorous stirring, 80 g of NaOH (30%) in such a way that the temperature does not exceed 30°, and stirring is maintained at 20° overnight. The toluene phase is then separated, and the reaction product is extracted with about 400 ml of ice-cold aqueous 1 N HCl. An amount of animal charcoal is added to the aqueous acid extract, and filtration is performed. The filtrate is rendered alkaline, in the presence of ice, with NaOH, and the oil which has precipitated is taken up with ether. The ether phase is washed with water, dried, and then concentrated by evaporation to dryness to yield 50 g (65% of theory) of N-(S-sec.-butyl-O-ethyl-thiophosphoryl)-N'-ethylguanidine in the form of light-yellow oil, $n_D^{20}=1.5110$ [Compound No. 34].

| | | |
|---|---|---|
| (1) | $nC_3H_7S-\underset{\underset{S}{\|\|}}{\overset{}{P}}(OC_2H_5)-NH-\underset{\underset{NH}{\|\|}}{\overset{}{C}}-NH-CN$ | m.p. 108°–110° |
| (2) | $nC_3H_7S-\underset{\underset{S}{\|\|}}{\overset{}{P}}(OC_2H_5)-N=\underset{\underset{NH_2}{\|}}{\overset{}{C}}-NH_2$ | m.p. 123°–126° |
| (3) | $nC_3H_7S-\underset{\underset{S}{\|\|}}{\overset{}{P}}(OC_2H_5)-N=\underset{\underset{NH_2}{\|}}{\overset{}{C}}-NH-isoC_4H_9$ | |
| (4) | $CH_3CH_2-CH(CH_3)-S-\underset{\underset{S}{\|\|}}{\overset{}{P}}(OC_2H_5)-N=\underset{\underset{NH_2}{\|}}{\overset{}{C}}-NH_2$ | oil |
| (5) | $nC_3H_7S-\underset{\underset{S}{\|\|}}{\overset{}{P}}(OC_2H_5)-N=\underset{\underset{NH_2}{\|}}{\overset{}{C}}-NH-CO-CH_3$ | $n_D^{20} = 1{,}5640$ |
| (6) | $nC_3H_7S-\underset{\underset{S}{\|\|}}{\overset{}{P}}(OC_2H_5)-N=\underset{\underset{NH_2}{\|}}{\overset{}{C}}-NH-CH_3$ | $n_D^{20} = 1{,}5745$ |
| (7) | $nC_3H_7-S-\underset{\underset{S}{\|\|}}{\overset{}{P}}(OC_2H_5)-N=\underset{\underset{NH_2}{\|}}{\overset{}{C}}-NH-CO-(CH_2)_4-CH_3$ | $n_D^{20} = 1{,}5230$ |

-continued

| # | Structure | Property |
|---|---|---|
| (8) | nC$_3$H$_7$—S\\ \ \ \ \ \ \ \ \ \ \ \ \ \ \ \ P(=S)—N=C(NH$_2$)—NH—CH$_3$\ /\ C$_2$H$_5$O | $n_D^{20} = 1{,}5745$ |
| (9) | nC$_3$H$_7$—S\\ \ \ \ \ \ \ \ \ \ \ \ \ \ \ \ P(=S)—N=C(NH$_2$)—NH—CO—C$_6$H$_5$\ /\ C$_2$H$_5$O | m.p. 85°–88° |
| (10) | nC$_3$H$_7$—S\\ \ \ \ \ \ \ \ \ \ \ \ \ \ \ \ P(=S)—N=C(NH$_2$)—NH—CO—(cyclohexyl-H)\ /\ C$_2$H$_5$O | m.p. 73°–75° |
| (11) | nC$_3$H$_7$S\\ \ \ \ \ \ \ \ \ \ \ \ \ \ \ \ P(=O)—NH—C(=NH)—NH—CO—NH$_2$\ /\ C$_2$H$_5$O | m.p. 174°–175° |
| (12) | nC$_3$H$_7$S\\ \ \ \ \ \ \ \ \ \ \ \ \ \ \ \ P(=O)—NH—C(=NH)—NH—CN\ /\ C$_2$H$_5$O | m.p. 142°–144° |
| (13) | nC$_3$H$_7$S\\ \ \ \ \ \ \ \ \ \ \ \ \ \ \ \ P(=O)—N=C(NH$_2$)—NH—nC$_4$H$_9$\ /\ C$_2$H$_5$O | $n_D^{20} = 1{,}5073$ |
| (14) | nC$_3$H$_7$S\\ \ \ \ \ \ \ \ \ \ \ \ \ \ \ \ P(=O)—N=C(NH$_2$)—N(CH$_3$)—CH$_3$\ /\ C$_2$H$_5$O | $n_D^{20} = 1{,}5222$ |
| (13) | nC$_3$H$_7$S\\ \ \ \ \ \ \ \ \ \ \ \ \ \ \ \ P(=O)—N=C(NH$_2$)—NH—nC$_4$H$_9$\ /\ C$_2$H$_5$O | $n_D^{20} = 1{,}5073$ |
| (14) | nC$_3$H$_7$S\\ \ \ \ \ \ \ \ \ \ \ \ \ \ \ \ P(=O)—N=C(NH$_2$)—N(CH$_3$)—CH$_3$\ /\ C$_2$H$_5$O | $n_D^{20} = 1{,}5222$ |
| (15) | nC$_3$H$_7$S\\ \ \ \ \ \ \ \ \ \ \ \ \ \ \ \ P(=O)—N=C(NH$_2$)—NH$_2$\ /\ C$_2$H$_5$O | m.p. 105°–107° |
| (16) | nC$_3$H$_7$S\\ \ \ \ \ \ \ \ \ \ \ \ \ \ \ \ P(=O)—N=C(NH$_2$)—NH—CO—CH$_3$\ /\ C$_2$H$_5$O | m.p. 133°–136° |
| (17) | CH$_3$CH$_2$CH(CH$_3$)—S\\ \ \ \ \ \ \ \ \ \ \ \ \ \ \ \ P(=O)—NH—C(=NH)—NH—CN\ /\ C$_2$H$_5$O | m.p. 138°–140° |
| (18) | CH$_3$CH$_2$CH(CH$_3$)—S\\ \ \ \ \ \ \ \ \ \ \ \ \ \ \ \ P(=O)—N=C(NH$_2$)—NH$_2$\ /\ C$_2$H$_5$O | m.p. 91°–93° |
| (19) | nC$_3$H$_7$—S\\ \ \ \ \ \ \ \ \ \ \ \ \ \ \ \ P(=O)—NH—C(=NH)—NH—CO—C(CH$_3$)$_3$\ /\ C$_2$H$_5$O | m.p. 84°–85° |
| (20) | (CH$_3$)$_2$CH—CH$_2$—S\\ \ \ \ \ \ \ \ \ \ \ \ \ \ \ \ P(=O)—NH—C(=NH)—NH—CN\ /\ C$_2$H$_5$O | m.p. 145°–147° |
| (21) | nC$_4$H$_9$—S\\ \ \ \ \ \ \ \ \ \ \ \ \ \ \ \ P(=O)—NH—C(=NH)—NH—CN\ /\ C$_2$H$_5$O | oil |

-continued

| | | |
|---|---|---|
| (22) | isoC₃H₇—S\P(=O)(OC₂H₅)—NH—C(=NH)—NH—CN | oil |
| (23) | nC₃H₇—S\P(=O)(OCH₃)—NH—C(=NH)—NH—CN | oil |
| (24) | isoC₃H₇—S\P(=O)(OC₂H₅)—N=C(NH₂)—NH—CO—(CH₂)₆—CH₃ | viscous |
| (25) | nC₃H₇—S\P(=O)(OC₂H₅)—N=C(NH₂)—NH—(CH₂)₇—CH₃ | viscous |
| (26) | nC₃H₇—S\P(=O)(OC₂H₅)—NH—C(NH₂)=NCO—C₆H₁₁ | m.p. 147°–148° |
| (27) | nC₃H₇—S\P(=O)(OC₂H₅)—NH—C(NH₂)=NCO(CH₂)₄—CH₃ | m.p. 101°–102° |
| (28) | nC₃H₇S\P(=O)(OC₂H₅)—N=C(NH₂)—NH—CO—C₆H₅ | m.p. 126°–129° |
| (29) | nC₃H₇S\P(=O)(OC₂H₅)—N=C(NH₂)—NH—CH(CH₃)CH₂CH₃ | $n_D^{20} = 1.5495$ |
| (30) | nC₃H₇S\P(=O)(OC₂H₅)—N=C(NH₂)—NHC₂H₅ | $n_D^{20} = 1.5142$ |
| (31) | nC₃H₇S\P(=S)(OC₂H₅)—N=C(NH₂)—NH—CH(CH₃)CH₂CH₃ | $n_D^{20} = 1.5056$ |
| (32) | CH₃CH₂CH(CH₃)—S\P(=O)(OC₂H₅)—NH—C(NH₂)=N—CO—(CH₂)₄CH₃ | m.p. 116° |
| (33) | CH₃CH₂CH(CH₃)—S\P(=O)(OC₂H₅)—NH—C(=NH)—NHCO—CH₃ | m.p. 152°–154° |
| (34) | CH₃CH₂CH(CH₃)—S\P(=O)(OC₂H₅)—N=C(NH₂)—NH—C₂H₅ | $n_D^{20} = 1.5110$ |
| (35) | (CH₃)₂CH—CH₂S\P(=O)(OC₂H₅)—N=C(NH₂)—NH₂ | m.p. ~ 30° |
| (36) | CH₃CH₂CH(CH₃)—S\P(=S)(OC₂H₅)—NH—C(=NH)—NHCN | oil |

-continued

(37)   
CH₃CH₂CH(CH₃)—S   
C₂H₅O—P(=O)—NH—C(=NH)—N(CN)—nC₄H₉   
$n_D^{20} = 1.5125$

(38)   
CH₃CH₂—CH(CH₃)—S   
C₂H₅O—P(=O)—NH—C(=NH)—N(CN)—CH₃   
$n_D^{20} = 1.5230$

(39)   
nC₃H₇—S   
C₂H₅O—P(=O)—NH—C(=NH)—N(CN)—CH(CH₃)—C₂H₅   
$n_D^{20} = 1.5150$

(40)   
nC₃H₇S, C₂H₅O—P(=O)—NH—C(=NH)—N(CN)(C₄H₉)   
$n_D^{20} = 1,5150$

(41)   
CH₃—CH₂—CH(CH₃)—S, C₂H₅O—P(=O)—N=C(NH₂)—NH—CH(CH₃)—CH₂CH₃   
$n_D^{20} = 1,5010$

(42)   
CH₃CH₂—CH(CH₃)—S, C₂H₅O—P(=O)—NH—C(=NH)—NH—CO—⬡—H   
m.p. 166°–168°

(43)   
C₃H₇S, C₂H₅O—P(=O)—NH—C(=NH)—N(CN)(CH₃)   
$n_D^{20} = 1,5270$

BIOLOGICAL EXAMPLES

EXAMPLE 6

Test to determine the nematocidal action

In order to test its action against soil nematodes, the active substance is added, at a concentration of 10 and 2.5 ppm, to soil and sand, respectively, infested with root-gall nematodes (Meloidogyne incognita), and thoroughly mixed in. In the soils prepared in this manner, there are planted immediately afterwards on the one hand tomato seedlings and on the other hand tobacco seedlings. An assessment of the nematocidal action is made, 28 days after planting, by counting the galls present on the roots.

Compounds of the formula I show in the above test a good action against Meloidogyne incognita, as can be seen from the mean values of three parallel tests. The assessment is based on the following scale of ratings:
0=0–5% infestation
1=5–25% infestation  2=25–80% infestation
3=above 80% infestation (ineffective)

The compounds of the formula I, inter alia Nos. 1, 2, 3, 4, 5, 7, 11 to 18, 26 to 29, 30, 32 to 34 and 36 to 43, have a good action (rating 0 to 1) with a concentration of active substance of 10 ppm.

The following known substances were tested for comparison. They were completely ineffective.

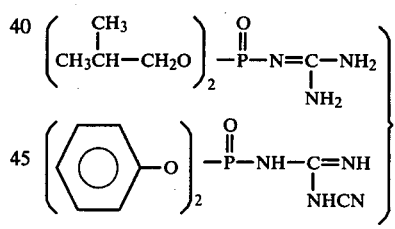

known from Houben-Weyl "Methoden der organischen Chemie", Vol. Phosphorverbindungen II, (Phosphorus compounds p.520

EXAMPLE 7

Action against fly maggots (Musca domestica)

An amount in each case of 50 g of freshly prepared CSMA nutrient medium for maggots was weighed off in beakers. Specific amounts of a 1% by weight acetonic solution of the respective active substance was transferred with a pipette to the nutrient medium in the beakers, so that concentrations of active substance in the nutrient medium of 0.1%, 0.05% and 0.01% were obtained. After a thorough mixing of the nutrient medium, the acetone was allowed to evaporate off for at least 20 hours. There were then placed into the beakers containing the nutrient medium thus treated in each case 25 one-day-old maggots of Musca domestica per active substance and concentration. After the maggots had pupated, the formed pupae were separated from the nutrient medium by washing out with water, and transferred to vessels closed by means of perforated lids. The pupae washed out in each case were counted (toxic effect of the active substance on the development of the maggots). There was then determined after 10 days the number of flies which had emerged from the pupae, and hence any occurring influence on metamorphosis ascertained.

Even at a low concentration, compounds of the formula I exhibited a good action.

EXAMPLE 8

Insecticidal action: Dysdercus fasciatus

Cotton plants were sprayed with an aqueous emulsion containing 0.05% of the compound to be tested (obtained from a 10% emulsifiable concentrate). After the coating had dried, the plants were infested with larvae of the species Dysdercus fasciatus in the $L_3$-stage. Two plants were used for each test compound, and the destruction rate obtained was determined after 2, 4, 8, 24 and 48 hours. The test was carried out at 24° C. with 60% relative humidity. Compounds Nos. 6, 15, 17, 18, 30, 33 and 35 effected after at the most 24 hours the complete destruction of larvae of the Dysdercus fasciatus species.

EXAMPLE 9

Insecticidal stomach-poison action/contact action: Anthonomus grandis

Potted cotton plants were sprayed with a spray liquor containing 500 ppm. of test substance (liquor prepared from a 25% wettable powder), and the applied liquor was allowed to dry. The plants were subsequently each infested with 5 one-day-old individuals of the Anthonomus grandis species, and the plants were kept in greenhouse compartments at 24° C. with 60% relative humdity. At intervals of 2, 4, 24 and 48 hours after the commencement of the test, the number of dead and dying insects was determined. Two plants were used for each test substance.

The compounds which exhibited in the test a good action against Anthonomus grandis (destruction between 4 and 24 hours) were, inter alia, the compounds Nos. 2, 6, 15, 17, 18, 30, 33 and 35.

EXAMPLE 10

Acaricidal action

Bean plants (Phaseolus vulgaris) were infested, 12 hours before the test, with an infested piece of leaf from a mass culture of Tetranychus urticae. The transferred mobile stages were sprayed with the emulsified test preparations from a chromatography-sprayer in a manner ensuring no overflow of the spray liquor. An assessment was made after 2 to 7 days at 25° C. in a greenhouse, by examination under a binocular microscope, of the living and of the dead larvae, adults and eggs. Compounds of the formula I exhibited a high degree of effectiveness against adults and larvae of Tetranychus urticae. Compounds Nos. 2, 5, 6, 7, 20, 30 to 35, 40, 41 and 42 effected after 2 days a complete destruction.

EXAMPLE 11

Bactericidal action against Xanthomonas oryzae on rice

Rice plants of the "Caloro" variety were watered, after 3-weeks' cultivation in a greenhouse, with a suspension or emulsion of the test substance (concentration of the test substance relative to pot soil = 100 ppm of active substance). Two days later, the same plants were sprayed, until dripping wet, with the test substance in the form of a spray liquor (concentration: 1000 ppm of active substance). To effect a better wetting of the plants, an adhesive and a wetting agent were added to the spray liquor. After one day's drying of the spray-coating, the rice plants were transferred to a greenhouse compartment at 24°-26° C. and 70-80% relative humdity, and then infested by cutting off the tips of the leaves with scissors which had previously been dipped into a bacteria suspension. After 8-days' incubation in the same compartment, there appeared characteristic symptoms of infection on the leaves. The extent of this area of infection served as a basis of evaluation for the effectiveness of the test substance.

The effectiveness is evaluated according to the following scale:

0 = 0-5% infestation
1 = 5-25% infestation
2 = 25-50% infestation
3 = >50% infestation (ineffective - infestation as on control plants)

The compounds of the formula I, inter alia, Nos 13, 14, 16, 30 and 34 attained the rating 0 or 1.

FORMULATION EXAMPLES

EXAMPLE 12

Dust:

The following substances are used to produce (a) a 5% dust and (b) a 2% dust:
(a) 5—parts of active substance, and
  95—parts of talcum;
(b) 2—parts of active substance,
  1—part of highly dispersed silicic acid, and
  97—parts of talcum.

The active substances are mixed and ground with the carriers, and in this form can be applied by dusting.

EXAMPLE 13

Granulate:

The following substances are used to produce a 5% granulate:
  5—parts of active substance,
  0.25—part of epichlorohydrin,
  0.25—part of cetyl polyglycol ether,
  3.50—parts of polyethylene glycol, and
  91—parts of kaolin (particle size 0.3-0.8 mm).

The active substance is mixed with epichlorohydrin and dissolved with 6 parts of acetone; polyethylene glycol and cetyl polyglycol ether are then added. The solution thus obtained is sprayed onto kaolin, and the acetone is subsequently evaporated off in vacuo. A microgranulate of this kind is advantageously used for combating nematodes.

EXAMPLE 14

Wettable powder:

The following constituents are used to produce (a) a 70% wettable powder, (b) a 40% wettable powder, (c) and (d) a 25% wettable powder, and (e) a 10% wettable powder:
(a)—70 parts of active substance,
  5 parts of sodium dibutylnaphthylsulphonate,
  3 parts of naphthalenesulphonic acid/phenolsulphonic acid/formaldehyde condensate 3:2:1,
  10 parts of kaolin, and
  12 parts of Champagne chalk;
(b)—40 parts of active substance, 5 parts of sodium lignin sulphonate,
1 part of sodium dibutylnaphthalenesulphonate, and
54 parts of silicic acid;
(c)—25 parts of active substance,
4.5 parts of calcium lignin sulphonate,
1.9 parts of Champagne chalk/hydroxyethylcellulose mixture (1:1),
1.5 parts of sodium dibutylnaphthalenesulphonate,
19.5 parts of silicic acid,
19.5 parts of Champagne chalk, and
28.1 parts of kaolin;
(d)—25 parts of active substance
2.5 parts of isooctylphenoxy-polyoxyethylene-ethanol,
1.7 parts of Champagne chalk/hydroxyethylcellulose mixture (1:1),
8.3 parts of sodium aluminium silicate,
16.5 parts of kieselguhr, and
46 parts of kaolin; and
(e)—10—parts of active substance,
3—parts of a mixture of the sodium salts of saturated fatty alcohol sulphates,
5—parts of naphthalenesulphonic acid/formaldehyde condensate, and
82—parts of kaolin.

The active substances are intimately mixed in suitable mixers with the additives, and the mixture is then ground in the appropriate mills and rollers. There are obtained wettable powders which have excellent wetting and suspension properties and while can be diluted with water to give suspensions of the desired concentration. These can be used in particular for leaf application.

EXAMPLE 15

Emulsifiable concentrate:

The following substances are used to produce a 25% emulsifiable concentrate:
25—parts of active substance,
2.5—parts of epoxidised vegetable oil,
10—parts of an alkylarylsulphonate/fatty alcohol polyglycol ether mixture,
5—parts of dimethylformamide, and
57.5 parts of xylene.

Emulsions of the desired application concentration can be prepared from these concentrates by dilution with water.

I claim:

1. A compound of the tautomeric formulae I

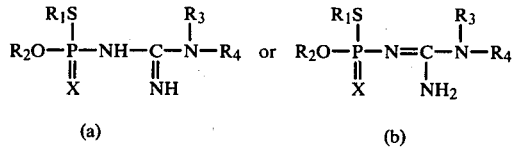

(a)    (b)

wherein
R$_1$ represents C$_3$-C$_5$-alkyl,
R$_2$ represents methyl or ethyl,
R$_3$ and R$_4$ independently of one another represent hydrogen, C$_1$-C$_8$-alkyl, CN, —CONH$_2$ acetyl, trimethylacetyl, propionyl, butyryl, valeryl, pivaloyl, caproyl, heptoyl, capryl, benzoyl or hexahydrobenzoyl, and X represents oxygen or sulphur.

2. A compound according to claim 1, wherein X represents oxygen.

3. A compound according to claim 1, wherein
R$_1$ represents C$_3$-C$_5$-alkyl,
R$_2$ represents ethyl,
R$_3$ represents hydrogen,
R$_4$ represents hydrogen, C$_1$-C$_8$-alkyl, CN acetyl, trimethylacetyl, propionyl, butyryl, valeryl, pivaloyl, caproyl, heptoyl, capryl, benzoyl or hexahydrobenzoyl, and
X represents sulphur.

4. A compound according to claim 1, wherein
R$_1$—represents C$_3$-C$_4$-alkyl,
R$_2$—represents ethyl,
R$_3$—represents hydrogen, and
R$_4$—represents the cyano group.

5. A compound according to claim 4, wherein X represents oxygen.

6. N-(S-sec.-Butyl-O-ethyl-thiophosphoryl)-N'-ethyl-guanidine of the formula

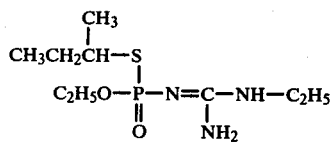

according to claim 1.

7. N-(S-sec.-Butyl-O-ethyl-thiophosphoryl)-N'-cyanoguanidine according to claim 1.

8. N-(S-n-Propyl-O-ethyl-thiophosphoryl)-N'-cyanoguanidine according to claim 1.

9. N-(S-sec.-Butyl-O-ethyl-dithiophosphoryl)-N'-cyano-guanidine according to claim 1.

10. A pesticidal composition which comprises as active ingredient an effective amount of a compound according to claim 1, together with a suitable carrier.

11. A composition according to claim 10 wherein the active ingredient is a compound according to claim 2.

12. A method of combating animal pests and microorganisms which comprises applying to their habitat an effective amount of a compound according to claim 1.

13. The method according to claim 12 wherein the pests are nematodes.

14. The method according to claim 12 wherein the pests are plant pathogenic nematodes.

15. A composition according to claim 10 wherein the active ingredient is a compound according to claim 3.

16. A composition according to claim 10 wherein the active ingredient is a compound according to claim 4.

17. A composition according to claim 10 wherein the active ingredient is a compound according to claim 5.

18. A compound according to claim 10 wherein the active ingredient is N-(S-sec.-butyl-O-ethyl-thiophosphoryl)-N'-ethyl-guanidine.

19. A composition according to claim 10 wherein the active ingredient is N-(S-sec.-butyl-O-ethyl-thiophosphoryl)-N'-cyano-guanidine.

20. A composition according to claim 10 wherein the active ingredient is N-(S-n-propyl-O-ethyl-thiophosphoryl)-N'-cyano-guanidine.

21. A composition according to claim 10 wherein the active ingredient is N-(S-sec.-butyl-O-ethyl-dithiophosphoryl)-N'-cyano-guanidine.

* * * * *